US010226624B2

(12) United States Patent
Dietz et al.

(10) Patent No.: US 10,226,624 B2
(45) Date of Patent: Mar. 12, 2019

(54) SOUND PROCESSING FOR A BILATERAL COCHLEAR IMPLANT SYSTEM

(71) Applicant: OTICON MEDICAL A/S, Smørum (DK)

(72) Inventors: Mathias Dietz, London (CA); Bradford Backus, Vallauris (FR)

(73) Assignee: Oticon Medical A/S, Smørum (DK)

( * ) Notice: Subject to any disclaimer, the term of this patent is extended or adjusted under 35 U.S.C. 154(b) by 302 days.

(21) Appl. No.: 15/187,865

(22) Filed: Jun. 21, 2016

(65) Prior Publication Data

US 2016/0367805 A1 Dec. 22, 2016

(30) Foreign Application Priority Data

Jun. 22, 2015 (EP) .................................... 15173203

(51) Int. Cl.
*A61N 1/00* (2006.01)
*A61N 1/36* (2006.01)
(Continued)

(52) U.S. Cl.
CPC ....... *A61N 1/36036* (2017.08); *A61N 1/0541* (2013.01); *H04R 25/552* (2013.01); *H04R 25/606* (2013.01); *H04S 2420/00* (2013.01)

(58) Field of Classification Search
CPC ............ A61N 1/36039; A61N 1/36036; A61N 1/0541; A61N 1/36038; H04R 25/554;
(Continued)

(56) References Cited

U.S. PATENT DOCUMENTS

2007/0016267 A1 1/2007 Griffin et al.
2010/0303267 A1 12/2010 Pedersen et al.
(Continued)

FOREIGN PATENT DOCUMENTS

WO WO 2014/194950 A1 12/2014

*Primary Examiner* — Mallika D Fairchild
(74) *Attorney, Agent, or Firm* — Birch, Stewart, Kolasch & Birch, LLP

(57) ABSTRACT

According to an embodiment, a method for producing stimulation pulses in a bilateral cochlear implant (CI) is disclosed. The method includes receiving a sound at a first microphone or a first microphone array positioned at or in the vicinity of a first ear of a user of the bilateral CI and receiving the sound at a second microphone or a second microphone array positioned at or in the vicinity of a second ear of the user of the bilateral CI. Furthermore, generating, using the first microphone or first microphone array, a first microphone signal in response to the sound received at the first microphone or first microphone array and generating, using the second microphone or second microphone array, a second microphone signal in response to the sound received at the second microphone or second microphone array. This is followed by filtering the first microphone signal into a plurality of band limited first microphone signals and a filtering the second microphone signals into a plurality of band limited second microphone signals. Later, determining a major sound based on analysis of the first microphone signal and/or the second microphone signal and/or at least one of the plurality of band limited first microphone signals and/or at least one of the plurality of band limited second microphone signals and extracting direction of arrival of the major sound. Based on the determined major source, a primary pulse pattern is generated and a secondary pulse pattern comprising for example a delayed and/or attenuated copy of the generated primary pulse pattern is then generated. The amount of delay and/or attenuation is based on the (Continued)

extracted direction of arrival. Finally, stimulating one cochlea using a primary stimulation pulse that is based on the primary pulse pattern and stimulating the other cochlea using a secondary stimulation pulse that is based on the secondary pulse pattern.

20 Claims, 6 Drawing Sheets

(51) Int. Cl.
  *A61N 1/05* (2006.01)
  *H04R 25/00* (2006.01)
(58) Field of Classification Search
  CPC .. H04R 25/505; H04R 25/552; H04R 25/356; H04R 25/407
  See application file for complete search history.

(56) References Cited

U.S. PATENT DOCUMENTS

| | | | |
|---|---|---|---|
| 2013/0336507 A1 | 12/2013 | Gran | |
| 2014/0219486 A1* | 8/2014 | Brown | H04R 25/43 381/320 |
| 2014/0330344 A1* | 11/2014 | Mishra | A61N 1/36032 607/57 |

* cited by examiner

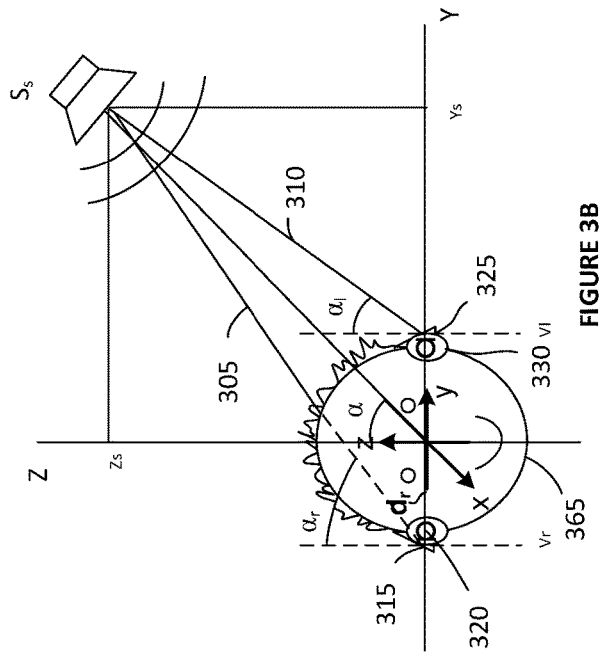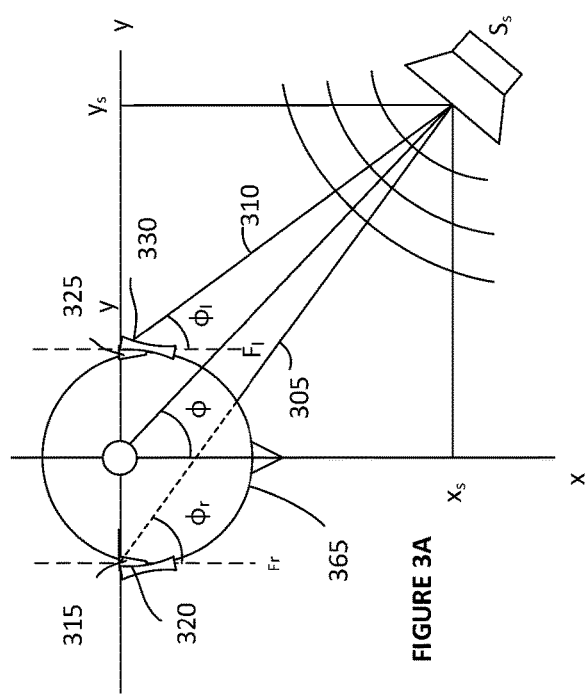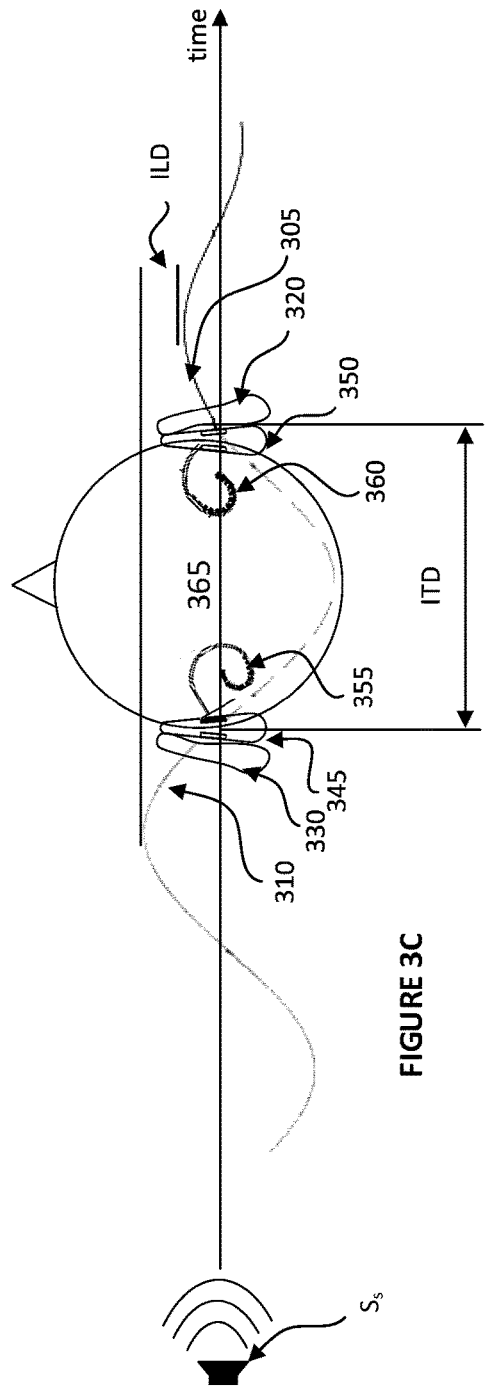
FIGURE 3B
FIGURE 3A
FIGURE 3C

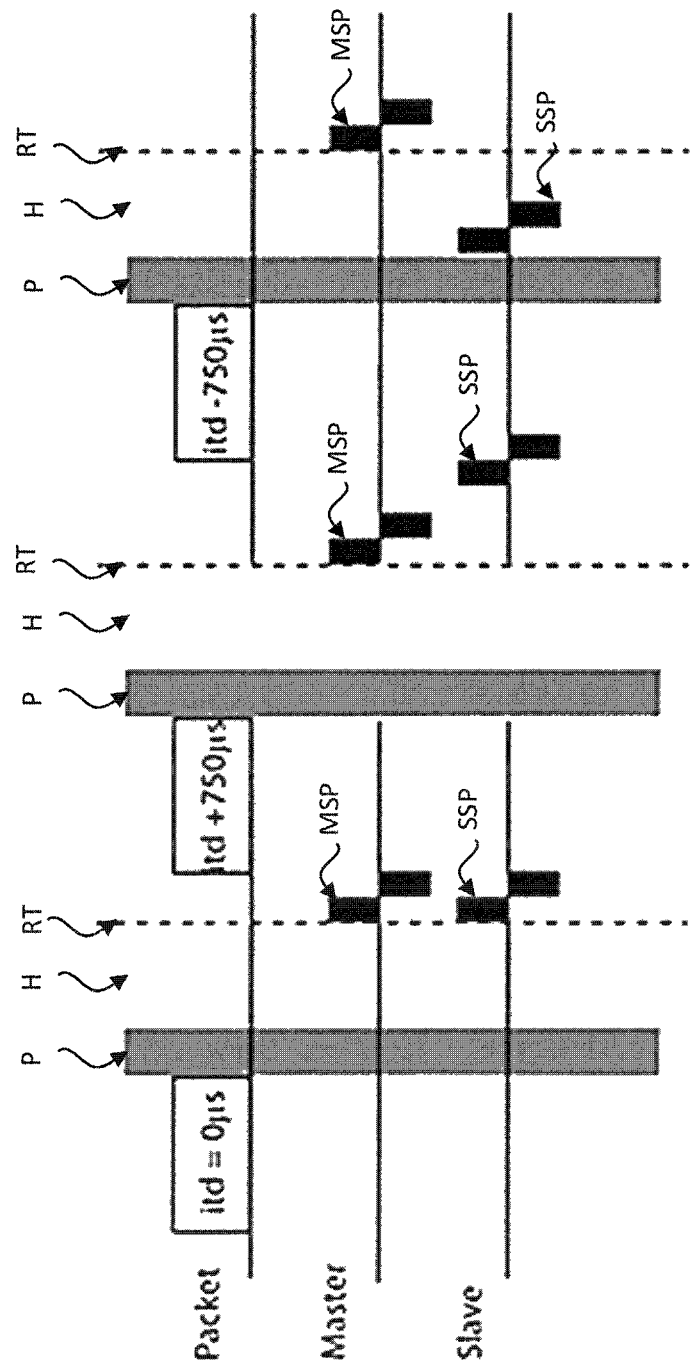

SOUND PROCESSING FOR A BILATERAL COCHLEAR IMPLANT SYSTEM

The work leading to this invention has received funding from the European Union Seventh Framework Programme (FP7/2007-2013) under grant agreement n° 304912.

FIELD

The disclosure relates to a sound processing method for a bilateral cochlear implant system. The disclosure also relates to a data transmission method used in the bilateral cochlear implant system. This includes methods for processing and delivering data used to improve sound source localization and/or enhance sound source salience by for example, introducing artificial binaural cues in a bilateral cochlear implant system.

BACKGROUND

A cochlear implant (CI) is a surgically implanted electronic device that provides a perception of sound to a person having a hearing impairment. In some people, cochlear implants may enable sufficient hearing for better understanding of speech. The quality of sound is different from natural hearing, with less sound information being received and processed by the brain.

Implanting both cochleas of hearing-impaired listeners with cochlear implants (referred to as bilateral cochlear implants) has become more common in recent years. Using binaural hearing in normal hearing listeners, i.e. where input along the auditory pathway after both ears are presented with the sound are integrated, boosts a person's ability to focus on speech in noisy situations, and allows a person to tune into sounds that are even low in level compared with the competing noise. There is thus a need for an effective system and method for providing these binaural benefits to hearing-impaired subjects, such as those subject that have bilateral cochlear implants.

Improving quality of life for CI users such as by prioritizing improving speech intelligibility in noise, sound localization, and pitch discrimination may require new types of information to be sent to and output by the CI implant.

One such new type of information that would help the CI users are binaural cues, i.e. synchronized information between the two ears. There are two main binaural cues for localizing sound in a plane of azimuth, i.e. angle of a sound source on the horizon relative to a point in the center of the head between the ears, namely (i) interaural time differences (ITDs), and (ii) interaural level differences (ILDs). ILDs are primarily a high-frequency cue, and occur because the listener's head shadowing the sound at the ear contralateral with respect to a sound source. Acoustically ITDs exist at all frequencies, however, normal hearing humans are typically most sensitive to ITDs at 500-900 Hz. In existing cochlear implant systems, the ITDs are not well-coded. It is expected that including such timing information will enhance spatial sound perception.

In an auditory environment (auditory scene) containing one or more sound sources (talkers or other sources of sound), individuals with normal hearing can utilize the binaural cues along with neural machinery for sound localization and to improve speech intelligibility in an auditory scene. One such auditory scene may include a talker (referred to as a target) spatially separated from a second talker (referred to as a masker), such as in the well-known "cocktail-party" problem.

Two normally functioning ears enable the human isolating spatially separated sources into different 'sound objects.' Consequently, normal hearing listeners can leverage this spatial separation to improve their speech reception of a target talker, provided that the competing noise sources are spatially separated from the target. Such an improvement in speech intelligibility is referred to in the art as a spatial release from masking (SRM).

Bilateral CI systems that aim to introduce this extra information need to develop a processing strategy that preserves or introduces this information appropriately and must also find a way to efficiently transmit this information to the implant system, for example utilizing transcutaneous data links. The data transmission problem is not a trivial one. In a bilateral system, the number of electrodes to command is doubled vs. a similar monaural system and extra information about the relationship between the two ears must be sent. Additionally, timing between the two electrode arrays need to be synchronized. Therefore, an efficient way to encode the synchronized ITD/timing data for both devices of a bilateral cochlear implant is needed. Reducing the amount of data to code this information will enable the data to be sent within the bandwidth budget of a transcutaneous data link and deliver an acceptable battery life for the patient.

SUMMARY

Cochlear Implant

A cochlear implant (CI) is a surgically-implanted prosthetic device that provides profoundly deaf with sensations of sound. A cochlear implant typically includes an external part that usually sits behind the ear and a second part that is surgically placed under the skin.

The external part usually includes a) a microphone for picking up the sound signal from the user's environment and generating the incoming microphone signal. The microphone may be placed at the ear or in the vicinity such as behind the ear, in the ear or canal, etc. b) a speech processor selects and processes sounds picked up by the microphone. The speech processor may include the filterbank, processing unit, determination unit, memory etc. and optionally c) a transmitter for transmitting processed microphone signal data such as the data like pulse pattern for generating implant electrode stimulation output. The second part usually includes a) an implanted receiver for receiving the transmitted stimulation data; b) an implanted stimulator such as a pulse generator, which allows the received stimulation data after processing such as charge mapping to be directed towards cochlea. In some embodiments, the data is sent using a series of stimulation pulse. The stimulator may also include a memory, and c) an electrode array comprising a group of electrodes implanted at specific insertion depths in the cochlea such that electrode position within the cochlea replicate or substantially replicate place-frequency mapping along length of cochlear of normal hearing. The electrodes receive the stimulation pulse corresponding to a particular frequency from the stimulator and send impulses via corresponding electrodes and subsequently by way of the auditory nerve to the brain, which recognizes the signals as sound.

The skilled person would appreciate that possible modifications in this generally described CI is possible. For example, a fully implantable CI where all components are implanted in the recipient/user of the cochlear implant is also possible. In this set up, a power source in the fully implantable CI may be inductively charged from outside of the CI recipient. In another example, fully implantable CI may still have the microphones in the external part in order to have better sound capturing capabilities compared to the microphones that are surgically implanted.

The bilateral cochlear implant system includes two implants—one positioned at each ear i.e. a left cochlear implant, and a right cochlear implant. In one embodiment, the left CI and right CI includes separate speech processors. However, in another embodiment, the left CI and the right CI share a common speech processor except for the microphones and their positioning. In both embodiments with separate or common speech processor, microphones relating to each ear are positioned at or in the vicinity of the respective ear, for example, a first microphone receiving sound arriving at the left ear and a second microphone receiving sound arriving at the right ear. The incoming microphone signals from microphones or microphone arrays positioned at each ear are provided to the respective speech processor, which may be a common speech processor. Similarly, the left CI and the right CI may also include separate or common implanted receiver.

Overview and Method

In several combinable embodiments, the disclosure discloses a sound processing method that utilizes determining a major sound and extracting direction of arrival of the major sound based on the sound received at a first microphone or first microphone array and a second microphone or second microphone array and to generate a primary pulse pattern and a secondary pulse pattern, which incorporates localization information based on the extracted direction of arrival. The pulse patterns are used to generate stimulation pulses for electrodes of each of the implanted electrode array. Several other techniques may also be implemented such as beamforming based on the extracted direction of arrival of the major sound, and application of gain to a received microphone signal level, etc. In other embodiments, the disclosure further discloses an efficient data transmission method wherein timing information, defining activation of the electrodes of each implanted electrode array for delivering the primary stimulation pulse and the secondary stimulation pulse at respective electrodes, is included either wholly in a data packet that is usually transcutaneously transmitted from the transmitter to one or more implanted receiver. Alternatively, the timing information is partially or wholly represented using arrival times of the pulses at the implanted second part such as at the receiver usually through transcutaneous transmission. In this implementation, few or no bits are dedicated to providing timing cues within the data packet, resulting in a more efficient data transmission. The details of these embodiments and other aspects of the disclosure are included in following description.

Thus, according to an embodiment, a method for producing stimulation pulses in a bilateral cochlear implant (CI) is disclosed. The method includes receiving a sound at a first microphone or a first microphone array positioned at or in the vicinity of a first ear of a user of the bilateral CI and receiving the sound at a second microphone or a second microphone array positioned at or in the vicinity of a second ear of the user of the bilateral CI. A first microphone signal is generated, using the first microphone or first microphone array, in response to the sound received at the first microphone or first microphone array and a second microphone signal is generated, using the second microphone or second microphone array, in response to the sound received at the second microphone or second microphone array. The first microphone signal is filtered into a plurality of band limited first microphone signals and the second microphone signals is filtered into a plurality of band limited second microphone signals. A major sound based on analysis of the first microphone signal and/or the second microphone signal and/or at least one of the plurality of band limited first microphone signals and/or at least one of the plurality of band limited second microphone signals is determined and direction of arrival of the major sound is extracted. A primary pulse pattern based on the determined major source is generated. Thereafter, a secondary pulse pattern comprising a copy of the generated primary pulse pattern and a localization information incorporated therein is generated. The localization information is based on the extracted direction of arrival. Lastly, an auditory nerve is stimulated using a primary stimulation pulse that is based on the primary pulse pattern and another auditory nerve is stimulated using a secondary stimulation pulse that is based on the secondary pulse pattern. In view of the bilateral CI, it is understandable that the auditory nerve is referred to the nerve on one side such as ipsilateral and the another auditory nerve on the other side such as contralateral.

In one embodiment, the primary pulse pattern based on the determined major source may be generated based on the first microphone signal and thus the primary pulse pattern relates to the electrode array associated with the first microphone or first microphone array. In this case, the secondary pulse pattern would relate to the electrode array associated with the second microphone or second microphone array. In an alternative embodiment, the primary pulse pattern based on the determined major source may be generated based on the second microphone signal and thus the primary pulse pattern relates to the electrode array associated with the second microphone or second microphone array. In this case, the secondary pulse pattern would relate to the electrode array associated with the first microphone or first microphone array. In a further embodiment, the primary pulse pattern and the secondary pulse pattern may be generated based on the same microphone signal and thus the primary pulse pattern and the secondary pulse pattern relate to the same microphone array. In this embodiment, the other microphone array can also be used for the signal processing but is not used directly to generate a pulse pattern.

Thus, the primary pulse pattern is dependent upon either the first microphone signal/one of the band limited first microphone signals and/or the second microphone signal/one of the band limited second microphone signals. Alternatively and preferably, the selection which microphone array forms the basis for the primary pulse pattern is dependent upon the microphone signal/band limited microphone signal of the microphone that is closer to the major sound. In yet another embodiment, the primary pulse pattern may be dependent upon a combination of the first microphone signal and second microphone signal or band limited first microphone signal and corresponding band limited second microphone signal. This is implement by employing a combining algorithm at a determination unit. The secondary pulse pattern may be generated using the copy of such primary pulse pattern with the localization information incorporated therein.

Beamformer

In an embodiment, the first microphone signal comprises a single channel output of the first microphone array using a beamforming algorithm utilizing the determined direction of arrival for beamsteering. Additionally or alternatively, the second microphone comprises a second microphone array and the second microphone signal comprises a single channel output of the second microphone array using the beamforming algorithm utilizing the determined direction of arrival for beamsteering. The method may be implemented with two separate beamforming units or a beamforming unit common to both the first microphone array and the second microphone array.

In general, such beamforming algorithms involve processing microphone signals received from the associated microphones array in such a way that the array acts as a highly directional microphone. In its simple version, it enhances signals from the front and suppresses signals from other directions. In a more sophisticated version, the enhancement direction can be set to the direction of the target sound "steering beamformer". In other words, beamforming provides a "listening beam" which points to, through e.g. beamsteering, the extracted direction of arrival, and receives, a particular sound source (dominant sound) while attenuating other sounds and noise, including, for example, reflections, reverberations, interference, and sounds or noise coming from other directions or points outside the primary beam. Various direction enhancement beamforming algorithms may be employed in order to improve quality of microphone signal of interest received from the dominant sound source. These algorithms may include, but not limited to, generalized sidelobe canceller (GSC), minimum variance distortionless response (MVDR), robust MVDR, or any other beamforming algorithm. Utilizing such beamforming algorithm based signal extraction techniques allows for creating favorable versions of microphone signal while at the same time attenuate or cancel other unwanted source signals received by the microphone array. Utilizing the direction of arrival information allows the setting of a steering direction and the binaural input allows a very efficient noise reduction with high directivity. For example, steering the beamformer towards target sound such e.g., from behind the user, in front of the user, or at the side of a user, e.g., in a car-cabin situation.

The CI user is usually better off with a maximally noise reduced input and with being constantly provided with localization information associated with the most dominant source.

Dominant Sound & Direction of Arrival

The localization information is dependent on an estimated direction of arrival of the major sound at the first microphone or microphone array and/or the second microphone or second microphone array.

In an embodiment, estimating the direction of arrival relies on combining microphone output signals from the left and right sides of the head to determine the delay between sounds present in the microphone outputs. When sounds emanate from the medial (front or rear) region of the wearer, there is little delay between the microphone output signals. However, this delay increases with increase in the angle of the sound source relative to the medial region. The delay increases from the medial region to either lateral region. This monotonic increase may be translated into direction of arrival of sounds with reference to the midline location between both ears. In another embodiment, the estimation technique relies on the shadowing effect of the human head. The head casts a shadowing effect for sounds located on opposite sides of the head. Due to this head shadowing effect, there may be noticeable level differences (in dB) between microphone output signals. The level difference increases as the sound source moves from the midline location between both ears to side. These two basic mechanisms may be used in direction of arrival algorithm estimation. For example, one such implementation for estimating the direction of arrival of a sound includes the steps of a) forming a reference signal, b) detecting sound with two or more spatially separated, directional or spatially separated directional, microphones to produce two or more output signals, c) calculating the relationships between each of the two or more output signals and the reference signal; and d) estimating the direction of arrival based on differences between the relationships. The reference signal may be formed by detecting sound with a dedicated reference signal microphone, which may be formed by way of a beamformer technique. The differences in the relationships may include the step of calculating interaural time differences, using a time correlation technique. The differences in the relationships may include the step of calculating interaural level differences using power difference measures. The step of calculating the relationships may be carried out across multiple frequency channels.

In another embodiment, the dominant sound source is identified by slicing the auditory scene surrounding the user into angular subspaces. A target signal detection and/or a voice activity detection on a respective spatial sound signal is performed, the spatial sound signal being generated by a spatial filter that divides sound received from the auditory scene in subspaces. Assuming the target signal to be present in a given subspace, the spatial sound signal of that subspace may have an improved target signal-to-noise signal ratio compared to sound signals which include the total space (i.e. the complete surrounding of a user), or other subspaces (not including the sound source in question). Further, the detection of several sound sources, e.g., talkers in different subspaces may be possible by running voice activity detection in parallel in the different subspaces.

Numerous techniques are known where left and right microphone signals is compared to derive a direction of arrival estimate. These techniques include; Correlation, Maximum Likelihood (covariance minimisation), Multiple Signal Classification (MUSIC), Estimation of Signal Parameters using Rotational Invariance Techniques (ESPRIT) or Eigen decomposition, and Matrix pencil using an array manifold or triangulation. An example includes a known technique for direction of arrival, which relies on sensory microphone arrays whereby the cross-correlation between the microphone output signals is calculated to determine the delay at which the maximum output power or peak occurs. Thus, the estimates reflect the direction of arrival of dominant sounds.

Many other known techniques are also discussed in cf. e.g. BELL, A. J. et al. *An information maximisation approach to blind separation and blind deconvolution. Neural Computation,* 1995, vol. 7 (6), 1129-1159; Jourjine, A. et al., *Blind separation of disjoint orthogonal signals: Demixing N sources from 2 mixtures.* IEEE International Conference on Acoustics, Speech, and Signal Processing (ICASSP 00), vol. 5, pp. 2985-2988, June 2000; ROWEIS, S. T. *One Microphone Source Separation.* Advances in neural information processing systems, 2001, 793-799; PEDERSEN, M. S. et al. *A survey of convolutive blind source separation methods.* Springer Handbook of Speech Processing. Springer, 2008, 1065-1094; BOLDT, J. B. et al. *Estimation of the ideal binary mask using directional systems.* IWAENC 2008, [Boldt et al., 2008] or combinations hereof, cf. e.g. PEDERSEN, M. S. et al. *Separating Underdetermined Convolutive Speech Mixtures.* ICA 2006, 2006, and [Boldt et al., 2008] PEREZ-LORENZO et al. *Evaluation of generalized cross-correlation method for direction of arrival estimation using two microphone in real environments. August* 2012, 73(8), Applied Acoustics (2012); PAULOSE et al. *Acoustic Source Localization.* Intl. Journal of Advanced Research in Electrical, Electronic and Instrumentation Engg. Vo. 2, Issue 2, February 2013.

Localization Information

In different embodiments, the sound localization information is dependent upon the determined direction of arrival of the major source. The localization information may be selected from a group consisting of an interaural difference, a modified interaural difference, an artificial interaural difference and a combination thereof.

In an embodiment, the interaural difference comprises an interaural time difference (ITD) and/or an interaural level difference (ILD). The interaural difference is determined between the one of the plurality of band limited first microphone signals and corresponding to one of the plurality of band limited second microphone signals. Depending on the direction of arrival, the major sound may arrive earlier at one ear of an individual than the other ear. This difference in time between when the sound arrives at one ear versus the other is referred to as the interaural time difference (ITD). The ILD is the difference in level (intensity) between a sound arriving at one ear versus the other, i.e. sound having higher level at ear closer to the sound source.

In one embodiment, the ILD is calculated as a level difference between the one of the band limited first microphone signal and one of the band limited second microphone signals. This may include using a level detector, as known in the art, that is configured to determine a first level of the one of the band limited first microphone signal, a second level of the one of the band limited second microphone signal, and a level difference between the first level and second level.

Additionally or alternatively, the ITD may be calculated as a difference between time-of-arrival of the major sound at the first microphone or first microphone array and time-of-arrival of major sound at the second microphone or second microphone array. Alternatively, once the direction of arrival of the major sound is extracted, the ITD may be computed by calculating the time of arrival of the major sound at one of the microphone or microphone array and utilizing a head related transfer function to estimate arrival time of the sound at another microphone or microphone array. This may be performed for at least one frequency band of related band limited microphone signals of the first microphone signal and second microphone signal. In several other embodiments, the LTD may be calculated based on signal analysis of the first microphone signal and the second microphone signal. According to one signal analysis embodiment, the ITD may be determined based on rate of change of the microphone/band limited microphone signals. Such implementation is available in a pending EP application numbered 15156861.5, which is incorporated herein by reference. In yet other signal analysis embodiments, instead of the rate of change of based estimation as disclosed in the referred pending EP application, the ITD may be determined using other known techniques based on a positive moving zero crossing of or peak extraction from microphone signal/band limited microphone signals.

In another embodiment, the sound localization information includes the modified interaural difference, which includes a modified interaural time difference (mITD) and/or a modified interuaral level difference (mILD). The modified interaural difference may be obtained by modifying the interaural difference (as described above) between the one of the plurality of band limited first microphone signals and corresponding one of the plurality of band limited second microphone signals. Such modifications may include at least one of amplifying the interaural difference, frequency shifting the interaural difference, representing the ITD as an ILD or representing the ILD as an ITD. For example, the amplification of the interaural difference may include increasing the delay between the onset time for activating an electrode of an electrode array and onset time for activating an electrode of the another electrode array compared to the determined ITD. Similarly, amplification may include increasing magnitude of the level difference as represented by increased difference in stimulation charges of the stimulation pulses compared to difference in electric charge that is based on the determined ILD. In other modifications such as in frequency transposition, the determined interaural difference, for example the ILD may be transposed to a lower frequency with or without amplification. The other listed modifications would be apparent to the skilled person and no further explanation is provided.

In yet another embodiment, the sound localization information includes an artificial interaural difference comprises an artificial interaural time difference (aITD) and/or an artificial interaural level difference (aILD). Based on the direction of arrival of the major sound, the artificial interaural difference may include a predetermined or dynamically selected value that allows for localizing the sound. It is apparent that once the direction of arrival of the major sound is extracted, the ear closer to and the ear farther away from the major source is known. Also, it is understandable that the ear closer to the major source may have a higher signal level relative to that of the ear farther away from the major source. Similarly, arrival of the sound at the ear closer to the major source will be earlier than that of the ear farther away from the major source. Hence, in an embodiment, the predetermined selected value may include a value such as X db interaural level difference and/or Y μs interaural time difference between the two ears. These predetermined values may also be frequency band specific, i.e. the corresponding band limited microphone signals of the first microphone signal and the second microphone signal. The aITD and/or aILD is not limited to naturally occurring ITDs or ILDs.

In another embodiment, the dynamically selected values for aILD and/or ITDs are algorithmically determined and may be based on one or more factors.

One such factor may be signal-to-noise ratio of the first microphone signal or band limited first microphone signal relative with that of the second microphone signal or corresponding band limited second microphone signal. Typically, the ear having a signal with a higher SNR may be considered closer to the major sound relative to the other ear.

Yet another factor may include a first horizontal angle (azimuth) that the major sound forms with a first front axis at the first ear and a second horizontal angle (azimuth) that the major sound forms with a second front axis at the second ear, such that ear forming a smaller angle with the major source is considered closer to the sound source. For example, if the first horizontal angle (azimuth) is smaller than the second horizontal angle (azimuth), then the first ear is closer to the sound source and vice versa. However, in a special scenario where the direction of arrival of the major sound is directly from side of one of the ears, i.e. the first angle and the second angle are equal, (90°). In this scenario, the algorithm may be configured to compare level of the first microphone signal or band limited first microphone signal with that of the second microphone signal or band limited second microphone signal and the ear corresponding to the signal having a higher level is determined as the ear closer to the sound source. The major sound forms a medial horizontal angle (azimuth) with a medial front axis. The medial front axis is typically parallel to the first front axis and the second front axis. In any of the disclosed embodiments, the value of localization information comprising aITD and/or aILD is configured to increase with an increase in the medial horizontal angle (azimuth). The algorithm may be configured to assign a value to the aITD/aILD as a function of the medial horizontal angle (azimuth), i.e. an increased value with an increase in the medial horizontal angle (azimuth).

Other factors may also be envisaged that allow to determine which ear is closer to the major sound. For example, yet another factor may include a first elevation angle that the major sound forms with a first vertical axis at the first ear and a second elevation angle that the major sound forms with a second vertical axis at the second ear, such that the ear forming a smaller elevation angle with the major source is considered closer to the sound source. For example, if the first elevation angle is smaller than the second elevation angle, then the first ear is closer to the sound source and vice versa. Once the ear closer to the major sound is determined, the algorithm is configured to dynamically assign a value such as X db interaural level difference and/or Y μs interaural time difference between the two ears. These dynamically assigned values may also be frequency band specific, i.e. the corresponding band limited microphone signals of the first microphone signal and the second microphone signal. The major sound forms a medial elevation angle with a medial vertical axis. The medial vertical axis is typically parallel to the first vertical axis and the second vertical axis. In any of the disclosed embodiments, the value of localization information comprising aITD and/or aILD is configured to increase with an increase in the medial elevation angle. The algorithm may be configured to assign a value to the aITD/aILD as a function of the medial elevantion angle, i.e. an increased value with an increase in the medial horizontal angle (azimuth).

In the above-recited embodiments, consideration is given to the actual angle measurement that the major sound forms with either the front axis or vertical axis to determined which of the horizontal angles or vertical angles is larger or smaller (later illustrated in Figures). The skilled person would realize that if the determination is based on obtuse angle measurement of the major sound with the front axis or vertical axis, then the criteria would reverse, i.e. the ear that forms a larger obtuse angle with the front axis or vertical axis is closer to the major sound. Irrespective of whether the predetermined value or dynamically selected value is chosen, the value is such that contrast between the perceptions of the sound arriving from two sides is increased, thus facilitating perception of sound localization to the user.

In yet another embodiment, a combination of the above-recited embodiments is also possible. For example, the primary pulse pattern and secondary pulse pattern may have an interaural difference comprising ILD and mITD, or aILD and ITD, or mILD and aITD, or other possible combinations.

Incorporating Localization Information

According to an embodiment, incorporation of the localization information in the copy of the primary pattern pulse includes increasing or decreasing stimulation level of the copy of the primary pattern pulse relative to stimulation level of the primary pulse pattern according to the determined ILD/modified ILD/artificial ILD. Such incorporation may also include a scenario where instead of modifying the level of the copy of the primary pulse pattern in accordance with the determined ILD/modified ILD/artificial ILD, the electric change of the secondary stimulation pulse is set in accordance with the determined ILD/modified ILD/artificial ILD and mapping function without the need to first modifying the level in the copy of primary pulse pattern.

In another embodiment, incorporation of the sound localization information in the copy of the primary pattern pulse includes associating early-activation or delayed-activation information, based on for example as the determined ITD/modified ITD/artificial ITD information, with the copy of the primary pulse pattern. For example, such information may be associated with arrival times of the primary pulse pattern and the secondary pulse pattern at the implant, wherein the difference in arrival times represent the determined ITD/modified ITD/artificial ITD information (described later). Thus, corresponding electrodes of two electrode arrays individually implanted in respective cochlea of the first ear and second ear are activated in accordance with a timing difference, as defined by the timing information that may include determined ITD/modified ITD/artificial ITD. In another embodiment, incorporation of the timing information may be provided as an information in a packet that is transmitted to the second part. At the second part, the received timing information may be utilized to determined time difference between activating an electrode of the electrode array and activating the corresponding electrode of the another electrode array.

In yet another embodiment, incorporation of the localization information includes a combination of earlier recited two embodiments describing level difference information and timing information.

Gain Application

In an embodiment, a gain may be applied either to the first microphone signal/one of the band limited first microphone signals and/or the second microphone signal/one of the band limited second microphone signals after the determination of the direction of arrival of the major sound. The gain may be applied prior to generation of the primary pulse pattern.

For example, the gain is applied to the microphone signal/band limited microphone signal that is generated by the microphone closer to the major sound. Applying the gain in this way, results in a larger signal-to-noise ratio improvement on the input signals such as from the binaural beamformer unit. Here the available direction of arrival information and the fact that microphone signals from both ears are available is very favorable.

Activating Electrodes of Electrode Arrays

Generally, each electrode of the plurality of electrodes of an electrode array (first or second electrode array) include a different frequency distribution as defined by a corresponding audio frequency range, usually referred as a stimulation channel. For example, the electrode array may include 20 implanted electrodes where electrode 1 close to the base of the cochlea associated with a frequency range between 6800 Hz to 8000 Hz, electrode 2 associated with a frequency range between 5800 Hz to 6800 Hz and so on with electrode 20 being closest to the apical region and covering frequency range between say 200 Hz to 300 Hz. It is apparent that the electrode array may include less or more than 20 electrodes and the frequency distribution for the electrodes may vary. The electrode array may include a ground electrode and may also include an additional electrode that is used for recording purposes only.

An electrode from the electrode array and an electrode from the another electrode array having an overlapping frequency distribution form the binaural electrode pair.

In an embodiment, a pulse generator (typically part of the implant/another implant) utilizes a signal level-electric charge mapping function and uses received primary pulse pattern and the secondary pulse pattern to generate the primary stimulation pulse and the secondary stimulation pulse. The mapping function may include a simple mapping function or an enhanced mapping function. The mapping function defines how target charge amounts for individual charge pulse in each pulse stream or auditory channel of a defined audio frequency range associated with the implanted electrodes may be computed from the determined stimulation level using linear or piecewise linear mapping function. Further disclosure on the simple mapping function and enhanced mapping function is available in FIG. 2 and related description in pending EP application numbered 15156861.5, which is incorporated herein by reference.

Thus, the primary stimulation pulse, based on the primary pulse pattern, adapted to stimulate an auditory nerve and a secondary stimulation pulse, based on the secondary pulse pattern, adapted to stimulate the another auditory nerve is generated.

The primary stimulation pulse activates an electrode of the electrode array implanted in an ear of the bilateral cochlear implant user whereas the secondary stimulation pulse activates the another electrode of the another electrode array implanted in the another ear of the bilateral cochlear implant.

In different embodiments, the proposed delay (representing ITD/mITD/aITD) may be result of difference in the arrival time of the primary pulse pattern (i.e. primary arrival time) at the implant/another implant or common receiver and arrival time of the secondary pulse pattern (i.e. secondary arrival time) at the another implant/the implant or common receiver or may be sent as a data packet information where ITD/mITD/aITD information is included. These implementations are described later.

N-of-M Pair

In an embodiment, the method includes selecting identical stimulation channels at an electrode array and the another electrode array such as employing N-of-M coding strategy. The selected stimulation channels is a subset of the channels available individually at the electrode array and the another electrode array. Thus, in this embodiment, for any given time frame, only N channels of the M channels, typically constant and equal to overall number of useable channels, are selected and selective narrow channel activation of the electrodes is employed to stimulate the auditory nerves. Thereby, the instantaneous stimulation rate of a selected channel is increased by a factor of M/N.

Such selection of identical stimulation channel may be based on a predetermined criteria such as channels having maximum energy.

In combination with the disclosed binaural pairing (described later), this embodiment may result in a shortlisted stimulation channels where one electrode of an array is a master electrode and the other electrode of the binaural pair is a slave electrode.

Transmission Method

In an embodiment, the generated primary pulse pattern and the generated secondary pulse pattern is transmitted from a processor to an implant and another implant respectively or to a common receiver. The common receiver is an implanted receiver that is common to both the electrode array and the another electrode array. Such transmission takes place prior to the stimulation of the auditory nerve and the another auditory nerve.

In an embodiment, the method includes transmitting, from the processor to an implant, the primary pulse pattern and localization information. The implant is configured to generate a copy of the received primary pulse pattern and incorporating the received localization information into the copy of the received primary pulse pattern to generate a secondary pulse pattern. The implant may also be configured to transmit the secondary pulse pattern from the implant to another implant. Alternatively, in another embodiment, the method includes transmitting, from the processor to an implant, the primary pulse pattern and transmitting, from the processor to an another implant, the primary pulse pattern or a copy of the primary pulse pattern along with the localization information. The another implant is configured to generate a secondary pulse pattern comprising the received primary pulse pattern with localization information incorporated therein.

ITD as Arrival Time

In one embodiment, a difference between a primary arrival time of the primary pulse pattern and a secondary arrival time of the secondary pulse pattern at the implant and another implant determines the activation times of an electrode of the electrode array and a corresponding electrode of the another electrode array respectively, the difference representing the ITD or mITD or aITD. In another embodiment, a difference between a primary arrival time of the primary pulse pattern and a secondary arrival time of the secondary pulse pattern at the common receiver determines the activation times of an electrode of the electrode array and a corresponding electrode of the another electrode array respectively, the difference representing the ITD or mITD or aITD. The common receiver is an implanted receiver that is common to both the electrode arrays.

Thus, the delay in activation of the electrodes of two electrode arrays may be implemented simply by an improved transmission method, where the arrival times of the pulse patterns determines a reference time for activating the primary electrode and a delay relative to the reference time, for example the artificial ITD, in receipt of the secondary pulse pattern or copy of primary secondary pulse pattern. Thus, the data to be transmitted is reduced by expressing desired electrode output timing data as the arrival time of a data message at the implant receiver. Thus, no bits are required to be included in a packet message to provide providing relative activation timing data in the data packet during the transmission. In order to produce proper timing cue, it is apparent that the processing time of the received primary pulse pattern and secondary pulse pattern is accounted for at the second part when utilizing this technique. Usually, the reference time may either follow directly after the processing delay or may be provided after a headroom that is provided after the processing delay.

In another implementation, the aITD and/or aILD may be included in a data packet that is transmitted from the processor.

Packet Transmission

In an embodiment, a data packet comprising information for generating the primary stimulation pulse and secondary stimulation pulse is transmitted from the processor to a receiver common to the implant and the another implant.

The data packet may include at least one of or a combination of any of
  ITD/modified ITD information/artificial ITD information, and primary stimulation pulse related level/charge information along with an ILD/modified ILD information/artificial ILD information, or primary stimulation pulse related level/charge information along with secondary stimulation pulse related level/charge information with ILD/modified ILD information/artificial ILD information incorporated therein; or
  a primary pulse pattern, a copy of the primary pulse pattern and the localization information.

Additionally, the packet may also include one or more of a header indicating arrival of a packet at the stimulator, binaural electrode pair information, n-of-m electrode information, and error checksum. For example, the packet may include the binaural pair information. Additionally or alternatively, the packet may include n-of-m-electrode information.

In this embodiment, the implant comprising the pulse generator utilizes the received information to generate the first stimulation pulse and the second stimulation pulse with the localization information incorporated therein in accordance with the method described above. The generated first stimulation pulse and the second stimulation pulse is then delivered to the electrode array and the another electrode array.

The embodiment disclosed in this section may also be utilized for a monaural cochlear implant where the electrodes from a base end and apex end of an implanted electrode array are paired, similar to the electrode pairing of the electrodes of the binaural electrode pair. The difference in packet arrival times would determine the activation timing for the electrodes at the base end and the apex end. Similarly, the stimulation pulse level information is transmitted as a packet from the processor to the receiver and utilized to generate the stimulation pulses.

According to an embodiment, during a transmission instant, the packet includes information relating to just two electrodes of a specific electrode pair. This is typically followed by transmitting a packet relating to another electrode pair.

Master—Slave Electrode Pair

In an embodiment, the method includes accessing a binaural electrode pair information comprising pairing of an electrode of an electrode array with an electrode of the another electrode array, wherein one electrode of the pair is a master electrode and another electrode is a slave electrode. In different embodiments, accessing the binaural electrode pair information may either be provided as part of the packet information or a look up table. The look up table may typically be stored in a memory of the bilateral cochlear implant, usually in a memory of the implanted second part. The binaural electrode pair information includes pairing of an electrode of the electrode array with an electrode of the another electrode array. Such pairing is usually based on the frequency distribution such an electrodes of a specific audio frequency range from first electrode array is paired with an electrode of corresponding, typically same, frequency range in the second electrode array. One of the electrode of the binaural pair may be pre-classified or dynamically assigned as the master electrode and another electrode of the binaural pair being pre-classified or dynamically assigned as the slave electrode.

In one scenario, the ILD is specified relative to the master electrode such that the slave electrode of the accessed binaural pair is activated with a higher electric charge compared to the correspondingly paired master electrode when the ILD is negative, but the master electrode array is activated with a higher electric charge compared to the correspondingly paired slave electrode when the ILD is positive. This is based on the calculation of the ILD with reference to the master, i.e. signal level of master–signal level of slave.

Additionally or alternatively, the ITD relative to the master electrode is specified such that the master electrode is activated at a reference time prior to the slave electrode when the ITD is positive, i.e. if the major sound arrives earlier at the microphone or microphone array corresponding to the master electrode. The reference time may follow directly after the processing delay. However, when the ITD is negative, i.e. the major sound arrives earlier at the microphone or microphone array corresponding to the slave electrode, then one of the two implementations may be applied.

In one implementation, the slave electrode is activated prior to the master electrode such that the master electrode is activated at the reference time and the slave electrode is activated utilizing a headroom, the headroom being provided prior to the reference time. The reference time may follow after the processing delay and directly after the headroom. In the second implementation, the master electrode is reassigned as a slave electrode and the slave electrode is reassigned as a master electrode, such that the reassigned master electrode is activated at the reference time and prior to the reassigned slave electrode without need of the headroom. Thus, the reference time may follow directly after the processing delay.

The processing delay is generally include time required to receive an incoming pulse pattern or packet, and processing the received pattern or packet to generate a related stimulation pulse. This may occasionally also include delivery time from pulse generator to an electrode of the electrode array. Thus, the reference time is the time at which the master/reassigned master electrode is activated.

In above embodiments, where ITD and ILD is specified relative to the master electrode; the dynamic allocation of the master electrode and slave electrode being based on predetermined criterion. For example, in an embodiment, electrode array associated with a microphone signal that shows a better signal-to-noise ratio includes electrodes that are dynamically assigned as the master electrode and the other one as the slave electrode in the binaural electrode pair. In other embodiments, similar dynamic allocation may be based on either horizontal angle (azimuth) or elevation angle, such angles being described earlier in the specification. Thus, a dynamic allocation of master and slave is made depending upon quality of sound reception at the first and second microphones.

Bilateral Cochlear Implant

According to an embodiment, a bilateral cochlear implant (CI) is disclosed. The bilateral cochlear implant includes a first microphone or a first microphone array, positioned at or in the vicinity of a first ear of a user of the bilateral CI, adapted to receive a sound and to generate a first microphone signal in response to the received sound. The implant also includes a second microphone or a second microphone array, positioned at or in the vicinity of a second ear of the user of the bilateral CI, adapted to receive the sound and to generate a second microphone signal in response to the received sound. A processor comprising a filter bank, a determination unit and a processing unit is also included in the bilateral cochlear implant. The filterbank adapted to filter the first microphone signal into a plurality of band limited first microphone signals and to filter the second microphone signal into a plurality of band limited second microphone signals. The determination unit adapted to determine a major sound based on analysis of the first microphone signal and/or the second microphone signal and/or at least one of the plurality of band limited first microphone signals and/or at least one of the plurality of band limited second microphone signals and to extract direction of arrival of the major sound. The processing unit adapted to generate a primary pulse pattern based on the determined major sound and to generate a secondary pulse pattern comprising a copy of the primary pulse pattern and a localization information incorporated therein, the localization information being based on the extracted direction of arrival. Lastly, the bilateral cochlear implant includes a pulse generator adapted to generate a primary stimulation pulse based on the primary pulse pattern for stimulating an auditory nerve and a secondary stimulation pulse based on the secondary pulse pattern for stimulating another auditory nerve.

In an embodiment, the system further includes a beamforming unit adapted to steer a listening beam of the first microphone array and/or the second microphone array towards the extracted direction of arrival of the major sound.

In another embodiment, a gain application unit is included. The unit is adapted to apply a gain to the first microphone signal/one of the band limited first microphone signals and/or to the second microphone signal/one of the band limited second microphone signals, prior to generating the primary pulse pattern.

In another embodiment, the system includes a transmitter adapted to transmit the primary pulse pattern and/or secondary pulse pattern and/or a copy of the primary pulse pattern and/or localization information from the processor to an implant and/or another implant and/or common receiver.

In another embodiment, the processor is adapted to control a primary arrival time and a secondary arrival time such that a difference between a primary arrival time of the primary pulse pattern and a secondary arrival time of the secondary pulse pattern at an implant and/or another implant and/or common receiver determines the activation times of an electrode of the electrode array and a corresponding electrode of the another electrode array respectively, the difference representing the ITD or mITD or aITD. The processor may typically be adapted account for the processing delays at the implant and/or another implant and/or common receiver such that the processing delay does not contribute in distorting the ITD or mITD or aITD. In other words, the processor is adapted to control the primary arrival time and the second arrival time as a function of difference in processing delays at the implant and/or another implant and/or common receiver.

In yet another embodiment, the processor is adapted to transmit, from the processor to a receiver common to the implant and another implant, a data packet comprising information for generating the primary stimulation pulse and secondary stimulation pulse. The data packet includes at least one of or a combination of any of ITD/modified ITD information/artificial ITD information, and primary stimulation pulse related level/charge information along with an ILD/modified ILD information/artificial ILD information, or primary stimulation pulse related level/charge information along with secondary stimulation pulse related level/charge information with ILD/modified ILD information/artificial ILD information incorporated therein; or a primary pulse pattern, a copy of the primary pulse pattern and the localization information.

Additionally, the packet may also include one or more of a header indicating arrival of a packet at the stimulator, binaural electrode pair information, n-of-m electrode information, and error checksum. For example, the packet may include the binaural pair information. Additionally or alternatively, the packet may include n-of-m-electrode information.

The bilateral cochlear implant system may include any of the features that are disclosed earlier in this disclosure.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. The individual features of each aspect may each be combined with any or all features of the other aspects. These and other aspects, features and/or technical effect will be apparent from and elucidated with reference to the illustrations described hereinafter in which:

FIG. 3A illustrates a first horizontal angle (azimuth) and a second horizontal angle (azimuth) according to an embodiment of the disclosure;

FIG. 3B illustrates a first elevation angle and a second elevation angle according to an embodiment of the disclosure;

FIG. 3C illustrates the principle of interaural time difference and interaural level difference;

FIG. 4A illustrates ITD based electrode activation relationship between a master electrode and a slave electrode when ITD=0 according to an embodiment of the disclosure;

FIG. 4B illustrates ITD based electrode activation relationship between a master electrode and a slave electrode when ITD=+ve according to an embodiment of the disclosure;

FIG. 4C illustrates ITD based electrode activation relationship between a master electrode and a slave electrode when ITD=−ve according to an embodiment of the disclosure;

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practised without these specific details.

Figure 1:
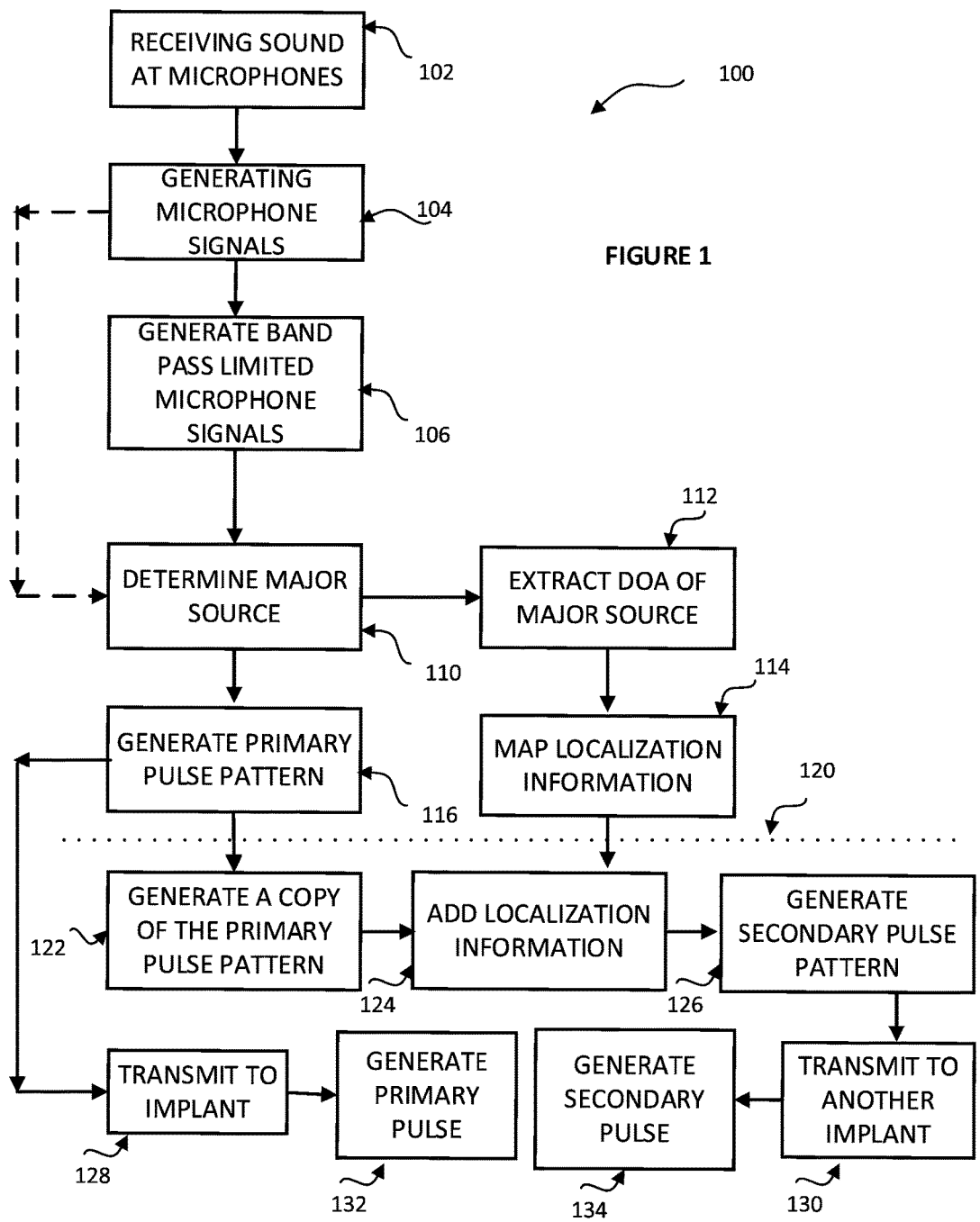
FIG. 1 illustrates a method for producing stimulation pulses in a bilateral cochlear implant according to an embodiment of the disclosure.

Referring to FIG. 1, illustrating a method 100 for producing stimulation pulses in a bilateral cochlear implant according to an embodiment of the disclosure. The method includes at 102 receiving a sound at a first microphone or a first microphone array positioned at or in the vicinity of a first ear of a user of the bilateral CI and receiving the sound at a second microphone or a second microphone array positioned at or in the vicinity of a second ear of the user of the bilateral CI. At 104, a first microphone signal is generated, using the first microphone or first microphone array, in response to the sound received at the first microphone or first microphone array and a second microphone signal is generated, using the second microphone or second microphone array, in response to the sound received at the second microphone or second microphone array. At 106, the first microphone signal is filtered into a plurality of band limited first microphone signals and the second microphone signals is filtered into a plurality of band limited second microphone signals. At 110, a major sound based on analysis of the first microphone signal and/or the second microphone signal and/or at least one of the plurality of band limited first microphone signals and/or at least one of the plurality of band limited second microphone signals is determined and at 112, a direction of arrival of the major sound is extracted. The extracted direction of major source is used to map localization information, which may include any of the or a combination of actual or modified or artificial ILDs or ITDs at 114. At 116, a primary pulse pattern based on the determined major source is generated. Thereafter, a copy of the generated primary pulse pattern is generated at 122 and the localization information incorporated therein at 124 to generate a secondary pulse pattern at 126. Lastly, the primary stimulation pulse, based on the primary pulse pattern and used to stimulate an auditory nerve, is generated at 132 and the secondary stimulation pulse, based on the secondary pulse pattern and used to stimulate another auditory nerve, is generated at 134.

In another embodiment, instead of utilizing the band limited microphone signals, the first microphone signal and second microphone signal may be used to determine the major source and the direction of arrival of the major source (as represented by the broken line in the FIG. 1).

In one embodiment, the primary pulse pattern is transmitted to an implant at 128 and the secondary pulse pattern is transmitted to another implant at 130 before the primary stimulation pulse and the second stimulation pulse are generated. In another embodiment, the transmission may include at 120, transmitting, from the processor to an implant, the primary pulse pattern and localization information. The implant is configured to generate a copy of the received primary pulse pattern and incorporating the received localization information into the copy of the received primary pulse pattern to generate a secondary pulse pattern, and transmitting the secondary pulse pattern from the implant to another implant. Alternatively, at 120, the transmission may include transmitting, from the processor to an implant, the primary pulse pattern and transmitting, from the processor to another implant, the primary pulse pattern or a copy of the primary pulse pattern along with the localization information. The another implant is configured to generate a secondary pulse pattern comprising the received primary pulse pattern with localization information incorporated therein.

Figure 2:
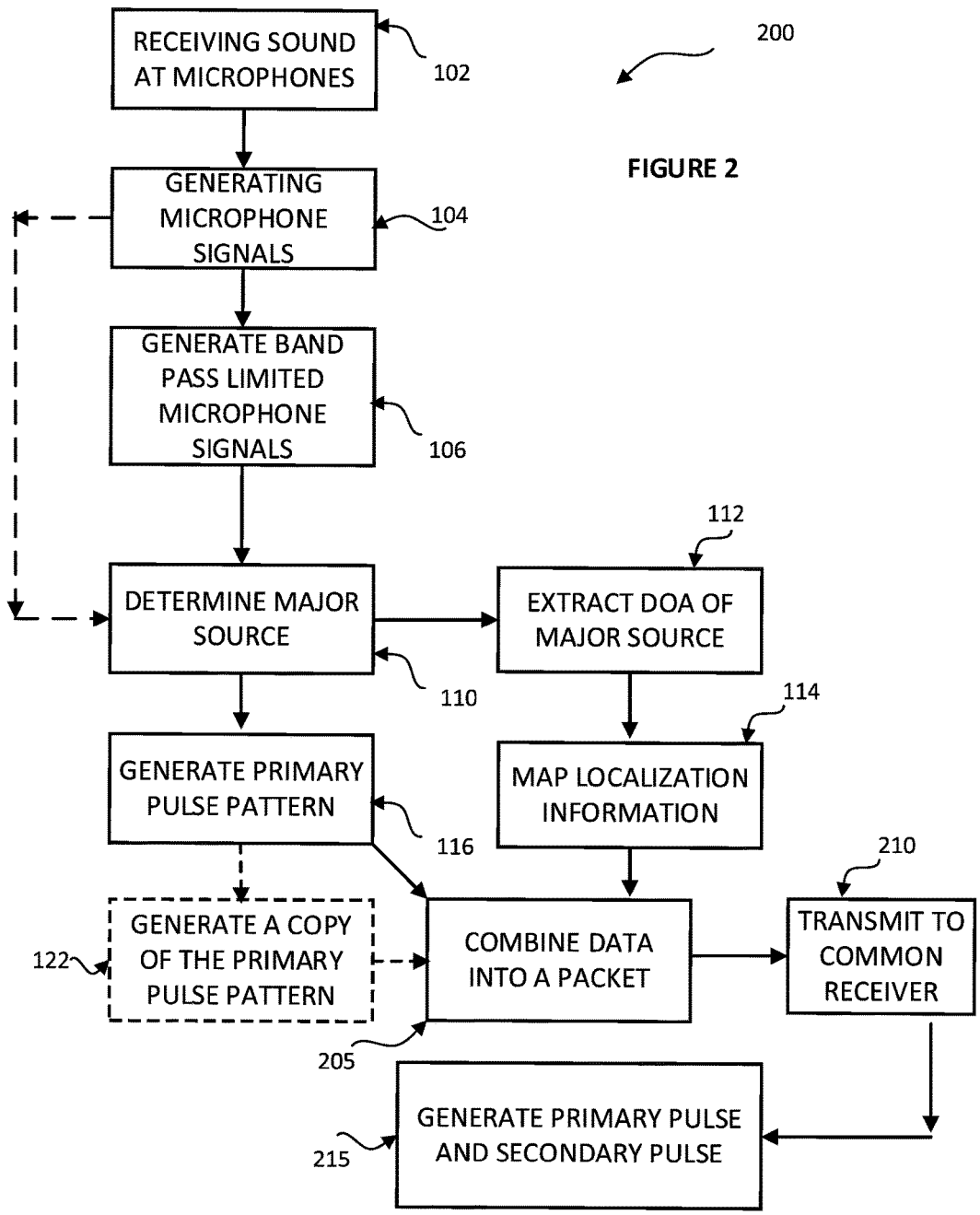
FIG. 2 illustrates a method for producing stimulation pulses in a bilateral cochlear implant according to another embodiment of the disclosure.

FIG. 2 illustrates a method 200 for producing stimulation pulses in a bilateral cochlear implant according to another embodiment of the disclosure. The method is substantially same as the method describing FIG. 1. However, after the generation of the primary pulse pattern at 116 and mapping localization information at 114, a data packet comprising information for generating the primary stimulation pulse and the secondary stimulation pulse is generated at 205. The data packet is transmitted from the processor to a receiver common to the implant and another implant at 210 and at 215, the primary stimulation pulse and the secondary stimulation pulse is generated based on the information available comprised in the received data packet.

In one embodiment, the data packet may include a primary pulse pattern, a copy of the primary pulse pattern and the localization information. In another embodiment, the data packet may include ITD/modified ITD information/artificial ITD information, and primary stimulation pulse related level/charge information along with an ILD/modified ILD information/artificial ILD information. In yet another embodiment, the data packet may include primary stimulation pulse related level/charge information along with secondary stimulation pulse related level/charge information with ILD/modified ILD information/artificial ILD information incorporated therein (as illustrated by broken lines where generation of packet is after the generation of the copy of the primary pulse pattern at 122).

It is apparent that once the direction of arrival of the major sound is extracted, the ear closer to and the ear farther away from the major source is known. Also, it is understandable that the ear closer to the major source may have a higher signal level relative to that of the ear farther away from the major source. Similarly, arrival of the sound at the ear closer to the major source will be earlier than that of the ear farther away from the major source. Hence, in an embodiment, the a value such as X db interaural level difference and/or Y µs interaural time difference between the two ears may be assigned either in a predetermined or a dynamic way. The allocation of such values may be based on factors like SNR, horizontal angle (azimuth), vertical angle at each ear.

FIG. 3A illustrates a first horizontal angle (azimuth) and a second horizontal angle (azimuth) according to an embodiment of the disclosure. The figure shows a user 365 having a first ear 330 with a first microphone (array) 325 in its vicinity and a second ear 320 with a second microphone (array) 315 in its vicinity. The sound source $S_s$ is located at a certain horizontal location with respect to the user such that the major sound 310 received at the first ear forms a first horizontal angle (azimuth) $\varphi_l$ with a first front axis $F_l$ at the first ear and the major sound 305 forms a second horizontal angle (azimuth) $\varphi_r$ with a second front axis $F_r$ at the second ear 320. The two front axis are parallel to each other and are defined as a line that runs along front-back of the user's head. The ear forming a smaller horizontal angle (azimuth) with the major source is considered closer to the sound source. For example, in the illustrated figure, the first horizontal angle (azimuth) is smaller than the second horizontal angle (azimuth) ($\varphi_l < \varphi_r$), thus the first ear 330 is closer to the sound source $S_s$ compared to the second ear 320. However, in a special scenario (FIG. 3C), where the direction of arrival of the major sound is directly from side of one of the ears, i.e. the first angle and the second angle are equal, (90°) and thus other means, such as level difference or time of arrival at the ear may be used to determine the ear closer to the sound source.

The major sound from the sound source $S_s$ forms a medial horizontal angle (azimuth) φ with a medial front axis. The medial front axis is typically parallel to the first front axis and the second front axis. In any of the disclosed embodiments, the value of localization information comprising aITD and/or aILD is configured to increase with an increase in the medial horizontal angle (azimuth).

FIG. 3B illustrates a first elevation angle and a second elevation angle according to an embodiment of the disclosure. The figure shows a user 365 having a first ear 330 with a first microphone (array) 325 in its vicinity and a second ear 320 with a second microphone (array) 315 in its vicinity. The sound source $S_s$ is located at a certain vertical location with respect to the user such that the major sound 310 received at the first ear forms a first elevation angle $\alpha_l$ with a first vertical axis $V_l$ at the first ear and the major sound 305 forms a second vertical angle $\alpha_r$ with a second vertical axis $V_r$ at the second ear 320. The two vertical axis are parallel to each other and are defined as a line that runs along height of the user's head. The ear forming a smaller vertical angle with the major source is considered closer to the sound source. For example, in the illustrated figure, the first horizontal angle (azimuth) is smaller than the second horizontal angle (azimuth) ($\alpha_l < \alpha_r$), thus the first ear 330 is closer to the sound source $S_s$ compared to the second ear 320.

The major sound from the sound source $S_s$ forms a medial elevation angle $\alpha$ with a medial vertical axis. The medial vertical axis is typically parallel to the first vertical axis and the second vertical axis. In any of the disclosed embodiments, the value of localization information comprising aITD and/or aILD is configured to increase with an increase in the medial elevation angle.

FIG. 3C illustrates the principle of interaural time difference and interaural level difference. The user 365 wears a first CI 345 comprising a first microphone (array) and an electrode array 355 at a first ear 330 and a second CI 350 comprising a second microphone (array) and second electrode array 360 at a second ear 320. The first microphone of the first CI receives sound 310 from a sound source $S_s$ that is positioned off set on one side of the ear, for example the sound coming from the left side of the user. The sound, represented by 305, is received at a second microphone of the second CI 350. The difference in arrival time of the sound at the first microphone and the second microphone is the interaural time difference (ITD) and the difference in level of the sound at the first microphone and the second microphone is the interaural level difference (ILD), which is because of the head shadow effect. In an embodiment, the estimation of the level and or arrival time of the sound at the ear allows for determination of the direction of arrival.

In accordance with an embodiment, one of the electrodes of an electrode array is defined as a master electrode and the corresponding electrode of another electrode array defined as a slave electrode. The master electrode and slave electrode form a binaural channel pair (paired electrode). The ITD parameter specifies the delay between the master and the slave electrode of a binaural channel pair (defined by the electrode pairing). The delay is specified relative to the master (i.e. slave=master+delay). The ITD delay can be either positive or negative, the positive indicating arrival of the major sound earlier at a microphone associated with the master electrode and negative indicating arrival of the major sound earlier at the microphone associated with the slave electrode. When the ITD is positive, the slave electrode is activated later than the master electrode (FIG. 3B). When the ITD is negative, the slave electrode is activated before the master electrode (FIG. 3C).

In one embodiment, at a reference time=0, which is defined as when the master is stimulated, there is a headroom H for example of 750 µs is or more but even less than 750 µs is also possible. The pulse generator is configured to generate the headroom H. This means an extra headroom is added to the overall latency of the time it takes from packet reception to producing activation on any electrode (master electrode) to allow for the possibility that the slave channel needs to be activated before the master electrode. In other words, a headroom is added to processing latency/delay so that after receipt of the packet, activation of the master and slave electrode may account for negative ITD.

FIG. 4A illustrates ITD based electrodes activation relationship between a master electrode and a slave electrode when ITD=0 according to an embodiment of the disclosure. In other words, both the first electrode array and the second electrode array are activated simultaneously. This may happen when the major sound is not offset with respect to the ears or the horizontal angles at the first ear and the second ear are equal such as the sound coming directly from front or behind. P represents the processing delay, H represents the headroom, MSP represents the stimulation pulse for the master electrode, SSP represents the stimulation pulse for the slave electrode, RT represents the reference time at which master electrode/reassigned master electrode is activated.

FIG. 4B illustrates ITD based electrodes activation relationship between a master electrode and a slave electrode when ITD=+ve according to an embodiment of the disclosure. In this embodiment, the master electrode array is activated prior to the slave electrode array by ITD/mITD/aITD which is represented by 750 µs. This may happen when the sound source is offset such that it is closer to the microphone corresponding to the master electrode. For example, if in FIG. 3A, electrode array 335 includes the master electrode.

FIG. 4C illustrates ITD based activation relationship between a master electrode and a slave electrode when ITD=−ye according to an embodiment of the disclosure. In this embodiment, the master electrode is activated at the reference time and the slave electrode array is activated prior to the master electrode, utilizing the headroom for prior activation. In this illustration, it is assumed that the ITD/mITD/aITD is 750 µs, which also represents the headroom facilitating such prior activation of the slave electrode. For example, this may happen when the major sound is closer to the microphone associated with the slave electrode.

In the illustrated FIG. 4, packet and pulse diagram show a headroom (H) required to produce 750 µs ITD. The headroom may be pre-assigned or may also be generated automatically. Other headroom values are also possible. P represents the fixed known processing delay and vertical broken line represents the reference time t=0 for master.

In an alternative embodiment, if the ITD=−ye, then instead of having a headroom based implementation, the master electrode is reassigned as a slave electrode and the slave electrode is reassigned as a master electrode. Hence, the reassigned master electrode is activated at the reference time and prior to the reassigned slave electrode, which is activated after the reassigned slave electrode. This implementation does not require the headroom and may be resembled as FIG. 4B (excluding the headroom) except that the MSP is reassigned master electrode and SSP is the reassigned slave electrode.

Figure 5:
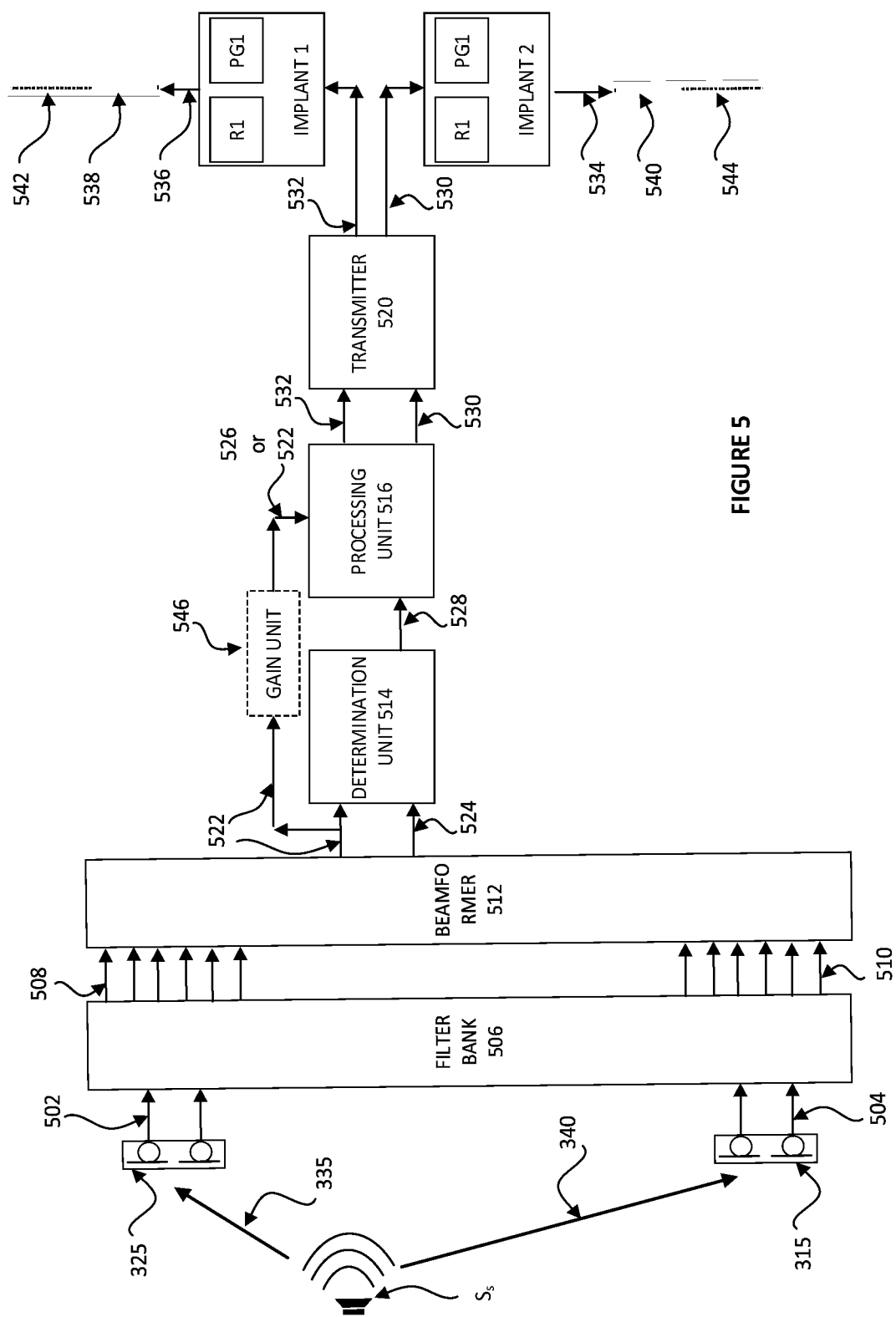
FIG. 5 illustrates a schematic diagram of a bilateral cochlear implant system according to an embodiment of the disclosure.

FIG. 5 illustrates a schematic representation of the bilateral cochlear implant in accordance with an embodiment of the disclosure. The bilateral cochlear implant (CI) includes a first microphone or a first microphone array 325, positioned at or in the vicinity of a first ear of a user of the bilateral CI. The first microphone or microphone array is adapted to receive a sound 335 and to generate a first microphone signal 502 in response to the received sound. A second microphone or a second microphone array 315 is positioned at or in the vicinity of a second ear of the user of the bilateral CI, adapted to receive the sound and to generate a second microphone signal 504 in response to the received sound. The bilateral CI also includes a processor a filterbank 506, with an optional beamformer 512, a determination unit 514 and a processing unit 516. The filterbank 506 is adapted to filter the first microphone signal 502 into a plurality of band limited first microphone signals 508 and to filter the second microphone signal 504 into a plurality of band limited second microphone signals 510. The optional beamformer 512 is adapted to produce highly noise reduced signals 522 and 524 from the signal 508 and corresponding band limited signal 510. The determination unit 514 is adapted to determine a major sound based on analysis of the first microphone signal and/or the second microphone signal and/or at least one of the plurality of band limited first microphone signals and/or at least one of the plurality of band limited second microphone signals and to extract direction of arrival of the major sound and to generate a single channel acoustic signal to generate the primary pulse pattern 532. The extracted direction of arrival information and localization information 528 is made available to the processing unit. The processing unit 516 is adapted to generate a primary pulse pattern 532 based on the determined major sound (either from 522 or 524) and to generate a secondary pulse pattern 530 comprising a copy of the primary pulse pattern and a localization information incorporated therein, the localization information being based on the extracted direction of arrival. An optional gain application unit 546 may be used to apply gain to the signal to generate an amplified signal 526 based on which the primary pulse pattern is generated (as illustrated by application of gain to signal 522). The generated primary pulse pattern 532 is transmitted using a transmitter 520 to a receiver R1 of an implant (Implant 1) where a pulse generator (PG1) generates, based on the primary pulse pattern, a primary stimulation pulse 536 that is delivered to an auditory nerve via an electrode 542 of an electrode array 538. Similarly, the generated secondary pulse pattern 530 is transmitted using the transmitter 520 to a receiver R2 of another implant (Implant 2) where a pulse generator (PG2) generates, based on the secondary pulse pattern, a secondary stimulation pulse 534 that is delivered to another auditory nerve via an electrode 544 of another electrode array 540.

The asymmetry in the path of sound 335 and 340 represents the difference in time of arrival (indicating distance as well) of the major sound from the sound source $S_s$ at the first microphone (array) and the second microphone (array) respectively. It is understandable that the sound source $S_s$ of the major sound is not part of the disclosed system but is the dominant sound source in the user's auditory scene.

The filter bank generally includes an array of frequency specific signal filters that separates the microphone signal into a plurality of band limited audio signals. Typically, the filter bank has a number of narrow frequency band filters with each filter associated with a specific band of audio frequencies. The incoming microphone signal is thus filtered into the plurality of band pass limited microphone signals where each signal corresponds to the band of frequencies for one of the band pass filters of the filter bank.

The determination unit 514 may include a level difference estimator configured to determine level difference between the signals 522 and 524 and/or a time difference estimator configured to estimate arrival time of the sound 335 at the first microphone (array) and that of the sound 340 at the second microphone (array). The determination unit may include a module configured to determine orientation of the user head in order to determine the medial horizontal axis and/or front axis and/or medial vertical axis and/or vertical axis. Furthermore, the determination unit may include modules configured to determine horizontal angles at the two ears and/or vertical angles at the two ears. The determination unit may include module adapted to determine SNR of the received signal 522 and 524 and to compare the determined SNRs as well.

The processing unit 516 may be adapted to control a primary arrival time and a secondary arrival time such that a difference between a primary arrival time of the primary pulse pattern and a secondary arrival time of the secondary pulse pattern at an implant and/or another implant and/or common receiver determines the relative activation times of an electrode of the electrode array and a corresponding electrode of the another electrode array respectively, the difference representing the ITD or mITD or aITD.

Figure 6:
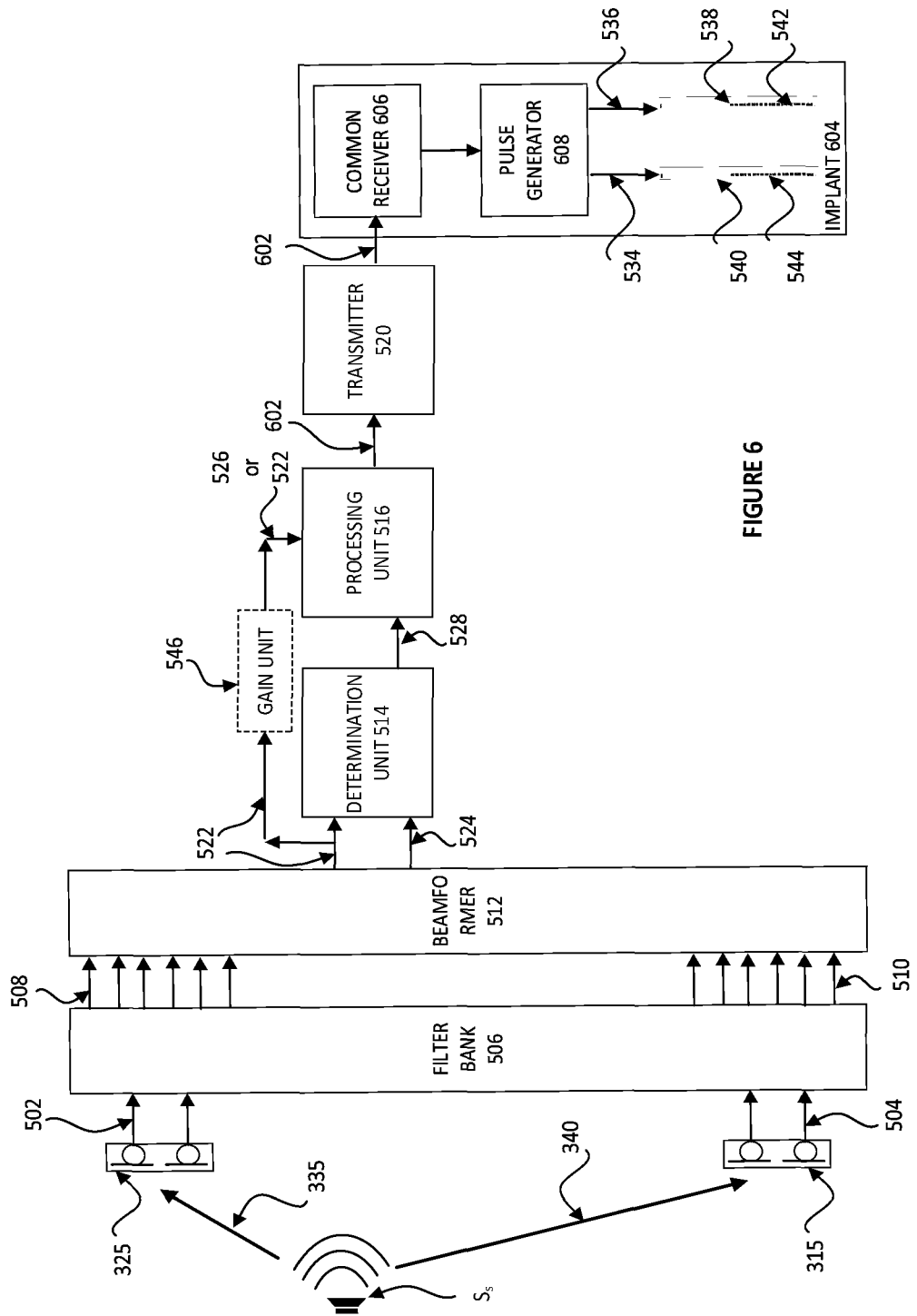
FIG. 6 illustrates a schematic diagram of a bilateral cochlear implant system according to an embodiment of the disclosure.

FIG. 6 illustrates a schematic representation of the bilateral cochlear implant in accordance with an embodiment of the disclosure. The features included in this embodiment are substantially same as the description of FIG. 5 except that instead of transmitting the primary pulse pattern and the second pulse pattern to the Implant 1 and Implant 2 respectively, a data packet 602 is transmitted using the transmitter 520 to a common receiver 606. The data packet includes information for generation of the primary stimulation pulse 536 and the secondary stimulation pulse 534. Thus, in this embodiment, the extracted direction of arrival information and localization information 528 is made available to the processing unit 516. The determination unit may be configured to provide level information about the signal 524 or the same can be obtained by the processing unit when the signal 524 is made available to the processing unit directly from the beamformer 524. The processing unit is configured to generate the data packet. The data packet includes at least one of or a combination of any of ITD/modified ITD information/artificial ITD information, and primary stimulation pulse related level/charge information along with an ILD/modified ILD information/artificial ILD information, or primary stimulation pulse related level/charge information along with secondary stimulation pulse related level/charge information with ILD/modified ILD information/artificial ILD information incorporated therein. The pulse generator 608 receives the information available in the data packet and is adapted to generate the primary stimulation pulse 536 that is delivered to an auditory nerve via an electrode 542 of an electrode array 538 and a secondary stimulation pulse 534 that is delivered to another auditory nerve via an electrode 544 of another electrode array 540.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

Accordingly, the scope should be judged in terms of the claims that follow.

We claim:

1. A method for producing stimulation pulses in a bilateral cochlear implant (CI), the method comprising:
receiving a sound at a first microphone or a first microphone array positioned at or in a vicinity of a first ear of a user of the bilateral CI and receiving the sound at a second microphone or a second microphone array positioned at or in a vicinity of a second ear of the user of the bilateral CI;

generating, using the first microphone or first microphone array, a first microphone signal in response to the sound received at the first microphone or first microphone array and generating, using the second microphone or second microphone array, a second microphone signal in response to the sound received at the second microphone or second microphone array;

filtering the first microphone signal into a plurality of band limited first microphone signals and filtering the second microphone signal into a plurality of band limited second microphone signals;

determining a major sound, and extracting a direction of arrival of the major sound, based on analysis of at least one of:
i) the first microphone signal and the second microphone signal, and
ii) at least one of the plurality of band limited first microphone signals and at least one of the plurality of band limited second microphone signals;

generating a primary pulse pattern based on the determined major sound;

generating a secondary pulse pattern comprising a copy of the generated primary pulse pattern and a localization information incorporated therein, the localization information being based on the extracted direction of arrival of the major sound at:
a) the first microphone or first microphone array, and
b) the second microphone or second microphone array; and generating a primary stimulation pulse that is based on the primary pulse pattern and generating a secondary stimulation pulse that is based on the secondary pulse pattern.

2. The method according to claim 1, wherein at least one of the following conditions is met:
the first microphone signal comprises a single channel output of the first microphone array using a beamforming algorithm utilizing the determined direction of arrival for beamsteering; and
the second microphone signal comprises a single channel output of the second microphone array using the beamforming algorithm utilizing the determined direction of arrival for beamsteering.

3. The method according to claim 1, wherein the localization information is dependent upon the determined direction of arrival of the major sound, the localization information is selected from any of an interaural difference, a modified interaural difference, an artificial interaural difference and a combination thereof.

4. The method according to claim 3, wherein
the interaural difference comprises at least one of an interaural time difference (ITD) and an interaural level difference (ILD), the interaural difference being determined between the one of the plurality of band limited first microphone signals and corresponding one of the plurality of band limited second microphone signals.

5. The method according to claim 3, wherein
the modified interaural difference comprises at least one of a modified interaural time difference (mITD) and a modified interaural level difference (mILD), the modified interaural difference being obtained by modifying the interaural difference between the one of the plurality of band limited first microphone signals and corresponding one of the plurality of band limited second microphone signals.

6. The method according to claim 3, wherein
the artificial interaural difference comprises at least one of an artificial interaural time difference (aITD) and an artificial interaural level difference (aILD), the artificial interaural difference being a predetermined or dynamically selected value that is dependent upon the determined direction of arrival of the major sound.

7. The method according to claim 1, further comprising, prior to the stimulation of the auditory nerve and the another auditory nerve, transmitting the generated primary pulse pattern and the generated secondary pulse pattern from a processor to:
an implant and an another implant respectively, or
a common receiver.

8. The method according to claim 1, further comprising transmitting, from the processor to an implant, the primary pulse pattern and localization information, the implant being configured to generate a copy of the received primary pulse pattern and incorporating the received localization information into the copy of the received primary pulse pattern to generate a secondary pulse pattern, and transmitting the secondary pulse pattern from the implant to another implant.

9. The method according to claim 1, further comprising transmitting, from the processor to an implant, the primary pulse pattern and transmitting, from the processor to an another implant, the primary pulse pattern or a copy of the primary pulse pattern along with the localization information, the another implant being configured to generate a secondary pulse pattern comprising the received primary pulse pattern with localization information incorporated therein.

10. The method according to claim 1, further comprising selecting identical stimulation channels at an electrode array and an another electrode array, the selected stimulation channels being a subset of the channels available individually at the electrode array and the another electrode array.

11. The method according to claim 1, further comprising transmitting, from the processor to a receiver common to the implant and the another implant, a data packet comprising information for generating the primary stimulation pulse and secondary stimulation pulse.

12. The method according to claim 11, wherein
a processor determines at least one of:
information of an interaural time difference (ITD), a modified ITD, or an artificial ITD, and
information of an interaural level difference (ILD), a modified ILD, or an artificial ILD,
the information for generating the primary stimulation pulse and secondary stimulation pulse, which is included in the data packet, is determined by the processor to include at least one of or a combination of any of:
1) the information of the ITD, the modified ITD, or the artificial ITD; primary stimulation pulse related level/charge information; and the information of the ILD, the modified ILD, or the artificial ILD;
2) the primary stimulation pulse related level/charge information along with secondary stimulation pulse related level/charge information with the information of the ILD, the modified ILD, or the artificial ILD incorporated therein; and
3) the primary pulse pattern, the copy of the primary pulse pattern and the localization information.

13. The method according to claim 1, wherein
a processor determines a difference between a primary arrival time of the primary pulse pattern and a secondary arrival time of the secondary pulse pattern at an implant and another implant
activation times of an electrode of the electrode array and a corresponding electrode of the another electrode array respectively are determined according to the difference between the primary arrival time and the secondary arrival time, and
the difference between the primary arrival time and the secondary arrival time represents an interaural time difference (ITD), or a modified interaural time difference (mITD) or an artificial interaural time difference (aITD).

14. The method according to claim 1, wherein
a processor determines a difference between a primary arrival time of the primary pulse pattern and a secondary arrival time of the secondary pulse pattern at a common receiver,
activation times of an electrode of the electrode array and a corresponding electrode of the another electrode array respectively,
the difference between the primary arrival time and the secondary arrival time represents an interaural time difference (ITD) or a modified interaural time difference (mITD) or an artificial interaural time difference (aITD).

15. The method according claim 1, further comprising
accessing a binaural electrode pair information comprising pairing, by a processor, of an electrode of the electrode array with an electrode of the another electrode array, wherein one electrode of the pair is pre-classified or dynamically assigned as a master electrode and another electrode as a slave electrode;
specifying, by the processor, an interaural level difference (ILD) relative to the master electrode such that when the ILD is positive, the master electrode array is activated with a higher electric charge compared to the correspondingly paired slave electrode and when the ILD is negative, the slave electrode of the accessed binaural pair is activated with a higher electric charge compared to the correspondingly paired master electrode.

16. The method according claim 1, further comprising
accessing a binaural electrode pair information comprising pairing, by a processor, of an electrode of the electrode array with an electrode of the another electrode array, wherein one electrode of the pair is pre-classified or dynamically assigned as a master electrode and another electrode as a slave electrode;
specifying an interaural time difference (ITD relative to the master electrode such that when the ITD is positive, the master electrode is activated at a reference time prior to the slave electrode and when the ITD is negative,
the slave electrode is activated prior to the master electrode such that the master electrode is activated at the reference time and the slave electrode is activated utilizing a headroom, the headroom being provided by the processor prior to the reference time; or
the master electrode is reassigned as a slave electrode and the slave electrode is reassigned as a master electrode, such that the reassigned master electrode is activated at the reference time and prior to the reassigned slave electrode without need of the headroom.

17. A bilateral cochlear implant (CI) comprising
a first microphone or a first microphone array, adapted to be positioned at or in a vicinity of a first ear of a user of the bilateral CI, adapted to receive a sound and to generate a first microphone signal in response to the received sound;
a second microphone or a second microphone array, adapted to be positioned at or in a vicinity of a second ear of the user of the bilateral CI, adapted to receive the sound and to generate a second microphone signal in response to the received sound;
a processor comprising
a filterbank adapted to filter the first microphone signal into a plurality of band limited first microphone signals and to filter the second microphone signal into a plurality of band limited second microphone signals;
a determination unit adapted to determine a major sound, and to extract direction of arrival of the major sound based on analysis of at least one of:
i) the first microphone signal and the second microphone signal, and
ii) at least one of the plurality of band limited first microphone signals and at least one of the plurality of band limited second microphone signals;
a processing unit adapted to generate a primary pulse pattern based on the determined major sound and to generate a secondary pulse pattern comprising a copy of the primary pulse pattern and a localization information incorporated therein, the localization information being based on the extracted direction of arrival of the major sound at:
a) the first microphone or first microphone array, and
b) the second microphone or second microphone array; and
a pulse generator adapted to generate a primary stimulation pulse based on the primary pulse pattern for stimulating an auditory nerve and a secondary stimulation pulse based on the secondary pulse pattern for stimulating another auditory nerve.

18. The bilateral cochlear implant according to claim 17, further comprising at least one of:
a beamforming unit adapted to steer a listening beam of at least one of the first microphone array and the second microphone array towards the extracted direction of arrival of the major sound; and
a gain application unit adapted to apply a gain to at least one of the first microphone signal, one of the band limited first microphone signals, the second microphone signal, and one of the band limited second microphone signals, prior to generating the primary pulse pattern; and
a transmitter adapted to transmit at least one of the primary pulse pattern, the secondary pulse pattern, a copy of the primary pulse pattern, and the localization information from the processor to at least one of an implant, another implant, and a common receiver.

19. The bilateral cochlear implant according to claim 17, wherein
the processor is adapted to control a primary arrival time and a secondary arrival time such that a difference between a primary arrival time of the primary pulse pattern and a secondary arrival time of the secondary pulse pattern at least one of an implant, another implant, and a common receiver is determinative of activation times of an electrode of the electrode array and a corresponding electrode of the another electrode array respectively, the difference representing an interaural time difference (ITD), a modified interaural time difference (mITD), or an artificial interaural time difference (aITD).

20. The bilateral cochlear implant according to claim 17, wherein
the processor is adapted to determine at least one of:
information of an interaural time difference (ITD), a modified ITD, or an artificial ITD, and
information of an interaural level difference (ILD), a modified ILD, or an artificial ILD,
the processor is further adapted to transmit, from the processor to a receiver common to the implant and another implant, a data packet comprising information for generating the primary stimulation pulse and secondary stimulation pulse, the data packet comprising at least one of or a combination of any of
1) the information of the ITD, the modified ITD, or the artificial ITD; primary stimulation pulse related level/charge information; and the information of the ILD, the modified ILD, or the artificial MD;
2) primary stimulation pulse related level/charge information along with secondary stimulation pulse related level/charge information with the information of the ILD, the modified ILD, or the artificial ILD incorporated therein; or
3) the primary pulse pattern, the copy of the primary pulse pattern and the localization information.

* * * * *